(12) United States Patent
Creighton, IV (10) Patent No.: US 7,305,263 B2
(45) Date of Patent: Dec. 4, 2007

(54) MAGNETIC NAVIGATION SYSTEM AND MAGNET SYSTEM THEREFOR

(75) Inventor: Francis M. Creighton, IV, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 537 days.

(21) Appl. No.: 10/801,062

(22) Filed: Mar. 15, 2004

(65) Prior Publication Data

US 2004/0249263 A1    Dec. 9, 2004

Related U.S. Application Data

(60) Provisional application No. 60/454,410, filed on Mar. 13, 2003.

(51) Int. Cl.
    *A61B 5/05*    (2006.01)
(52) U.S. Cl. ............ 600/424; 600/424; 600/425; 600/427; 600/429; 378/11; 378/13; 378/205; 606/130
(58) Field of Classification Search ........ 600/424–427, 600/429; 606/130; 378/11, 13, 205
    See application file for complete search history.

(56) References Cited

U.S. PATENT DOCUMENTS

| | | | |
|---|---|---|---|
| 6,241,671 B1 * | 6/2001 | Ritter et al. ............... | 600/427 |
| 6,630,879 B1 * | 10/2003 | Creighton et al. .......... | 335/306 |
| 6,975,197 B2 * | 12/2005 | Creighton, IV ............ | 335/306 |
| 7,019,610 B2 * | 3/2006 | Creighton et al. .......... | 335/306 |
| 2001/0038683 A1 * | 11/2001 | Ritter et al. ............... | 378/137 |
| 2003/0137380 A1 | 7/2003 | Creighton et al. | |
| 2004/0030324 A1 | 2/2004 | Creighton et al. | |
| 2004/0158972 A1 | 8/2004 | Creighton et al. | |
| 2004/0199074 A1 * | 10/2004 | Ritter et al. ............... | 600/424 |
| 2007/0038064 A1 * | 2/2007 | Creighton, IV ............ | 600/407 |
| 2007/0146106 A1 * | 6/2007 | Creighton et al. .......... | 335/285 |

* cited by examiner

*Primary Examiner*—Eleni Mantis Mercader
*Assistant Examiner*—A. Lauritzen
(74) *Attorney, Agent, or Firm*—Harness, Dickey & Pierce, P.L.C.

(57) ABSTRACT

A magnetic navigation system for orienting a magnetically responsive medical device in a selected direction within an operating region in a subject's body. The system includes a support for supporting the subject, a magnet system a magnetic field to the operating region, and an imaging system. The magnet system includes at least two magnets disposed on opposite sides of the operating region for applying a magnetic field of at least 0.08 Tesla in any selected direction in the operating region by a change of the position and/or orientation of the magnets within an exclusion zone volume. The imaging system includes an imaging beam source and an imaging beam detector disposed on opposite sides of the operating region. The source and the detector being carried on a C-arm which can pivot about an axis generally parallel to the longitudinal axis of the subject to change the imaging angle. The magnets of the magnet system being configured and positioned so that the C-arm can pivot through at least about 60° without impinging upon the exclusion zone of the magnets.

30 Claims, 5 Drawing Sheets

MAGNETIC NAVIGATION SYSTEM AND MAGNET SYSTEM THEREFOR

CROSS-REFERENCE TO PREVIOUSLY FILED APPLICATIONS

This invention claims priority of U.S. Patent Application Ser. No. 60/454,410, filed Mar. 13, 2003, the entire disclosure of which is incorporated herein by reference.

BACKGROUND OF THE INVENTION

This invention relates to a magnetic navigation system for applying a navigating magnetic field to an operating region inside a subject while simultaneously imaging the operating region.

Magnetic navigation systems have been developed which apply a navigating magnetic field in a selected direction to an operating region in a subject to change the direction of a magnetically responsive medical device in the operating region. Examples of such systems are disclosed in U.S. Pat. No. 6,241,671, issued Jun. 5, 2001, for Open Field System for Magnetic Surgery; and U.S. Pat. No. 6,630,879, issued Oct. 7, 2003, An Efficient Magnet System for Magnetically-Assisted Surgery, the disclosures of which are incorporated herein by reference. However for many procedures it is desirable to provide simultaneous or near simultaneous images of the operating region either to confirm the position and orientation of the medical device, or to otherwise control the medical procedure being conducted with the medical device. Imaging can be conveniently provided with a C-arm mounted x-ray imaging system, employing an imaging beam source and detector disposed on opposite sides of the operating region. However, the magnet systems employed in magnetic navigation systems typically must be positioned in close proximity to the subject in order to provide magnetic field of sufficient strength to be useful in navigation. Thus the magnet systems create an exclusion zone around the subject into which the imaging system cannot impinge, and this exclusion zone restricts the orientations at which the C-arm can be positioned for imaging.

SUMMARY OF THE INVENTION

In accordance with the principles of the present invention, a magnet navigation system for magnetically navigating within an operating region is provided in which a C-arm based imaging system can pivot at least about 60° around the operating region, and more preferably at least about 75°, still more preferably at least about 80°, and in some embodiments as much as 120°. Generally, a preferred embodiment of a magnetic navigation system in accordance with the principles of this invention is adapted to orient a magnetically responsive medical device in a selected direction within an operating region in a subject's body. The system generally comprises a support for supporting the subject, a magnet system for applying a magnetic field to an operating region in the subject, and an imaging system for imaging the operating region. The magnet system preferably comprise at least two magnets disposed on opposite sides of the operating region for applying a magnetic field of sufficient navigating strength in any selected direction in the operating region by a change of the position and/or orientation of the magnets within separate exclusion zones. The imaging system preferably comprises an imaging beam source and an imaging beam detector disposed on opposite sides of the operating region. The source and the detector are carried on a conventional C-arm which can pivot about an axis generally parallel to the longitudinal axis of the subject to change the angular position of the source and the detector, and thus the angle at which the operating region is imaged. The magnets of the magnet system are configured and positioned so that the C-arm can pivot through at least about 60° without impinging upon the exclusion zones of the magnets.

The magnets can be sized and shaped, and the imaging system carried on the C-arm can be selected so that pivoting ranges of as much as about 120° can be achieved. In some preferred embodiments the at least two magnets are directly opposed at 180° apart, and in other embodiments the at least two magnets are oriented at angles of between about 163° to about and about 178°. In some embodiments the at least two magnets can rotate around the operating zone (preferably in fixed relation to each other) to thereby move their exclusion zones to increase the pivot range of the C-arm.

The systems of the present invention provide magnet navigation of magnetically responsive devices in the body, while achieving an extended range of imaging angles of the operating region, to provide better information about the operating region for use in navigating medical devices and/or using medical devices in the operating region.

BRIEF DESCRIPTION OF THE DRAWINGS

FIG. 4A is a schematic view of an alternate implementation of the second embodiment in which the magnets can rotate about the operating region, showing a 120° range of motion for a C-arm carrying a 20 cm receiver, with the magnets rotated 22.5° in the opposite direction from its normal position;

DETAILED DESCRIPTION OF THE INVENTION

Figure 1:
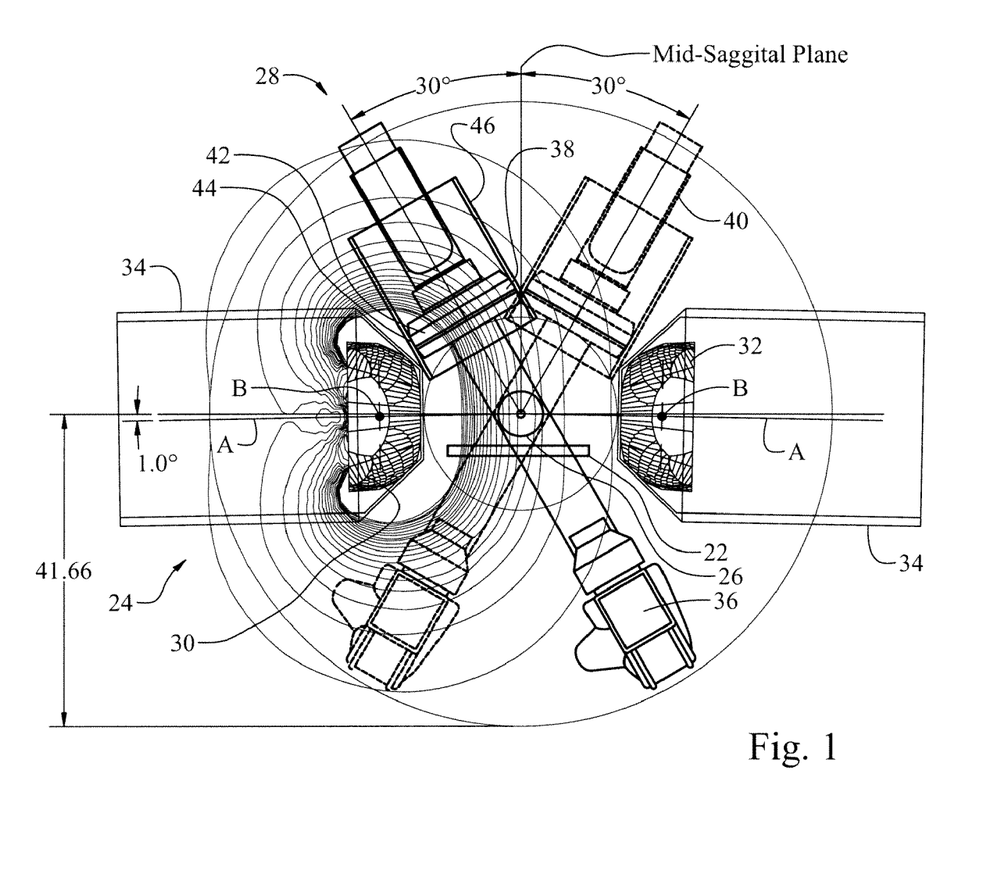
FIG. 1 is a schematic view of the arrangement of a first embodiment of a magnet system constructed according to the principles of this invention, showing a 60° range of motion for an imaging C-arm carrying a 30 cm×30 cm receiver plate.

A first embodiment of a magnetic navigation system constructed according to the principles of this invention is shown schematically in FIG. 1. The magnetic navigation system is adapted for orienting a magnetically responsive medical device in a selected direction within an operating region in a subject's body. The first embodiment of the system comprises a support 22 for supporting the subject, a magnet system 24 for applying a magnetic field to the operating region 26, and an imaging system 28 for imaging the operating region 26.

The subject support 22 is preferably a generally horizontal surface for supporting a subject in a generally horizontal position so that the operating region of the system is positioned within the subject's body.

The magnet system 24 comprises at least two magnets 30 and 32 disposed on opposite sides of the operating region 26 for applying a magnetic field sufficient for magnetic navigation in any selected direction within the operating region. (Magnet 30 is shown in FIG. 1 with its magnetic field lines, but for clarity, magnet 32 is shown without its magnetic field lines). Magnets 30 and 32 are preferably identical in construction. The strength of the field required for magnetic navigation depends in part upon the magnetic responsiveness of the device that is in the operating region 26, which is typically provided with a magnetically responsive element, such as a permeable or permanent magnet, or an electromagnetic device. In this preferred embodiment, the magnets 30 and 32 preferably can provide a navigating field of at least about 0.08 Tesla in any selected direction in the operating region, however in other embodiments the magnets 30 and 32 might be designed to provide a magnetic field of at least about 0.06 Tesla, or even lower as advances are made in improving the magnetic responsiveness of the medical devices deployed in the operating region 26. The magnets 30 and 32 are shaped and configured so that a change of the position and/or orientation of the magnets within an exclusion zone 34 permits the magnets to apply a magnetic field of the desired strength in the operating region 26 in any selected direction. A mechanism, not shown, is provided for repositioning and reorienting the magnets 30 and 32 as required to provide the desired field in the operating region. An example of one possible device is disclosed in U.S. patent application Ser. No. 10/347,525, for Magnetic Navigation System, incorporated herein by reference.

Each of the magnets is preferably made up of a plurality of blocks of magnetic material each of which is magnetized in one of a plurality of predetermined magnetization directions to maximize the magnet field in a particular direction at an operating point spaced from the front face of the magnet. It has been empirically determined that increments of 30° in magnetization direction are usually adequate, and any gains in field strength by obtained by smaller increments are usually not cost-effective. Details of the construction of such magnets are disclosed in U.S. Pat. No. 6,630,879, issued Oct. 7, 2003, An Efficient Magnet System for Magnetically-Assisted Surgery, and in U.S. patent application Ser. No. 10/056,227 for Rotating And Pivoting Magnet For Magnetic Navigation, the disclosures of which are incorporated herein by reference. The design of such magnets is disclosed in U.S. patent application Ser. No. 10/082,715 for Magnets With Varying Magnetization Direction and Method of Designing Such Magnets, incorporated herein by references. A possible method of manufacturing such magnets is disclosed in U.S. patent application Ser. No. 10/704,195, for Method of Making A Compound Magnet, incorporated herein by reference.

Each of the magnets 30 and 32 is sized and shaped to so that by translating the magnet along a first axis A extending radially from the operating region 26, pivoting of the magnet about a second axis B perpendicular to the first axis A and extending substantially through the center of mass of the magnet, and rotation of the magnet about the first axis A, permits the magnets 30 and 32 to apply a magnetic field to the operating region 26 in any selected direction. The translation, pivoting, and rotation of the magnets required to achieve the desired range of directions in the operating region define the exclusion zone 34 into which the imaging system 28 must not impinge so as to not interfere with the proper operation of the magnet system 24. In general the magnet is translated and pivoted to follow a line of constant magnetic field strength, e.g. the 0.08 Tesla line, at the operating point in the operating region. The rotation of the magnet allows the direction of the field to be changed. Pivoting the magnets at or near their centers of mass helps reduce the size of the exclusion zones 34, and also allows for more compact and less expensive mechanisms for pivoting the magnets.

As shown in the Figures, the exclusion zone 34 is generally cylindrical, with a frustoconical front face oriented toward the operating region 26. The exclusion zone is preferably contained within a protective shell, which protects the mechanism for moving the magnet, and hides the movement from view.

The imaging system 28 comprises an imaging beam source 36 and an imaging beam detector 38 disposed on opposite sides of the operating region 26. The source 36 and the detector 38 are carried on a C-arm 40 which can pivot about an axis generally parallel to the longitudinal axis of the subject on the support 22, to change the imaging angle of the operating region 26. (Two C-arms are shown in FIG. 1 in order to illustrate the range of motion of the C-arm, but there is preferably only one C-arm used for imaging the operating region 26).

The detector 38 is preferably a solid state amorphous silicon x-ray receiving plate 42, which is substantially unaffected by the magnetic fields created by the magnet system 24. These solid state receiving plates are presently available in 20 cm×20 cm and 30 cm×30 cm sizes, with the 30 cm×30 cm size being shown in FIG. 1. Of course some other size imaging plate could be used. The imaging plate is disposed in a cover 44, so that the width of the imaging zone extends 15 cm on either side of the centerline between the imaging source 36 and the imaging receiver 38 for a 20 cm×20 cm plate, and so that the width of the imaging zone extends 20 cm on either side of the centerline between the imaging source 36 and the imaging receiver 38 for a 30 cm×30 cm plate.

The receiving plate 42 is preferably mounted for translation toward and away from the operating region 26, in order to change the resolution of the images of the operating region. The movement of the receiving plate 42 and cover 44 define an imaging zone 46 extending generally from the operating region 26, centered along the line between the source 36 and the receiver 38 through the center of the operating region 26. As described below the magnet system, and in particular the exclusion zones of the magnet system, preferably does not impinge upon this imaging zone 46.

The magnets 30 and 32 are configured and positioned so that the C-arm 40 can pivot through at least about 60° without impinging upon the exclusion zone of the magnets, and more specifically, so that the magnets 30 and 32 and their exclusions zones 34 don't impinge upon the C-arm 40, the imaging beam source 36 and detector 38, or the imaging zone 46. Similarly, the C-arm 40, the imaging beam source 36 and detector 38, and the imaging zone 46 do not impinge upon the magnets 30 and 32 and their exclusions zones.

As shown in FIG. 1, rather than being in direct opposition, 180° apart, the magnets 30 and 32, and more particularly the first axes A of the magnets 30 and 32 intersect at an angle of 178°. This additional 2° permits the C-arm 40 to travel a full 60°. In the preferred embodiment, this travel is preferably symmetric about the mid-sagittal plane, so that the imaging system can provide left anterior oblique and right anterior oblique images at 30° from the mid-sagittal plane.

In some alternate constructions, the magnets 30 and 32 can be mounted for movement (preferably in fixed relationship to each other) about the operating region, to provide greater clearance for the imaging system to thereby extend the pivot range of the C-arm 40.

Figure 2:
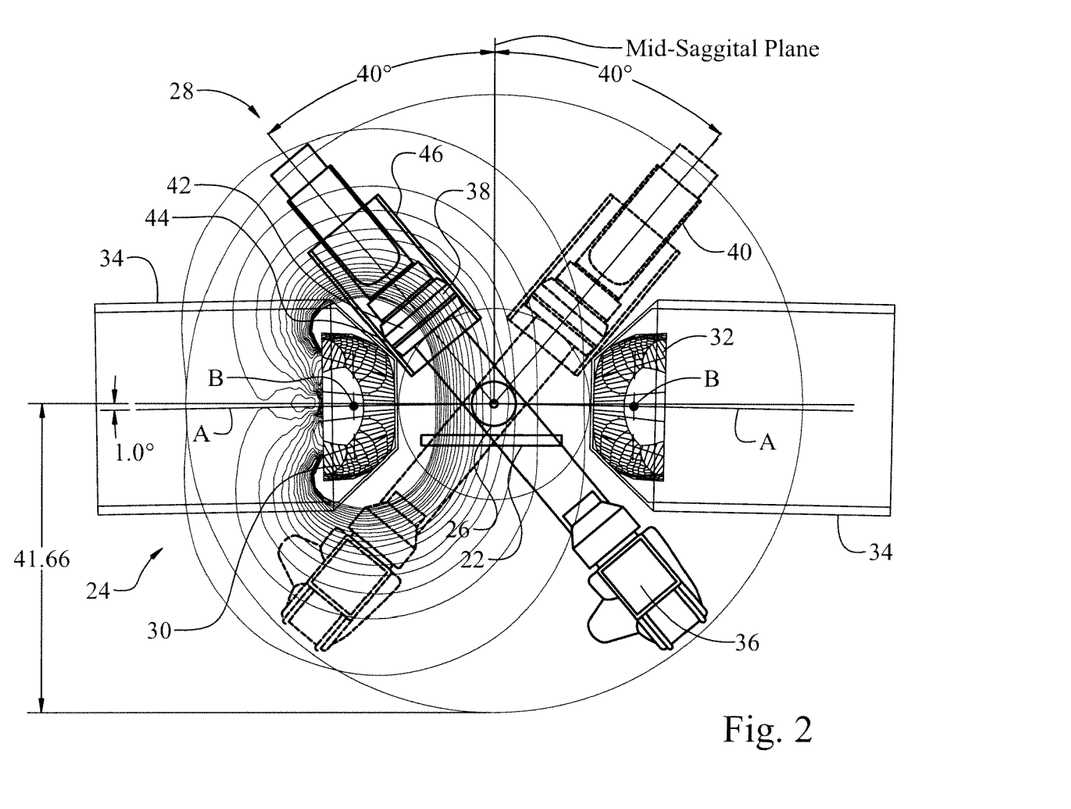
FIG. 2 is a schematic view of the first embodiment of the magnet system shown in FIG. 1, showing a 80° range of motion for an imaging C-arm carrying a 20 cm receiver.

As shown in FIG. 2, the imaging system can alternatively be provided with a 20 cm×20 cm imaging plate. The smaller imaging plate 42 results in a smaller imaging zone 46, and thus permits a broader range of pivoting of the C-arm. Thus, as shown in FIG. 2, the C-arm 40 can pivot over a range of 80°, preferably centered on the mid-sagittal plane.

Figure 3:
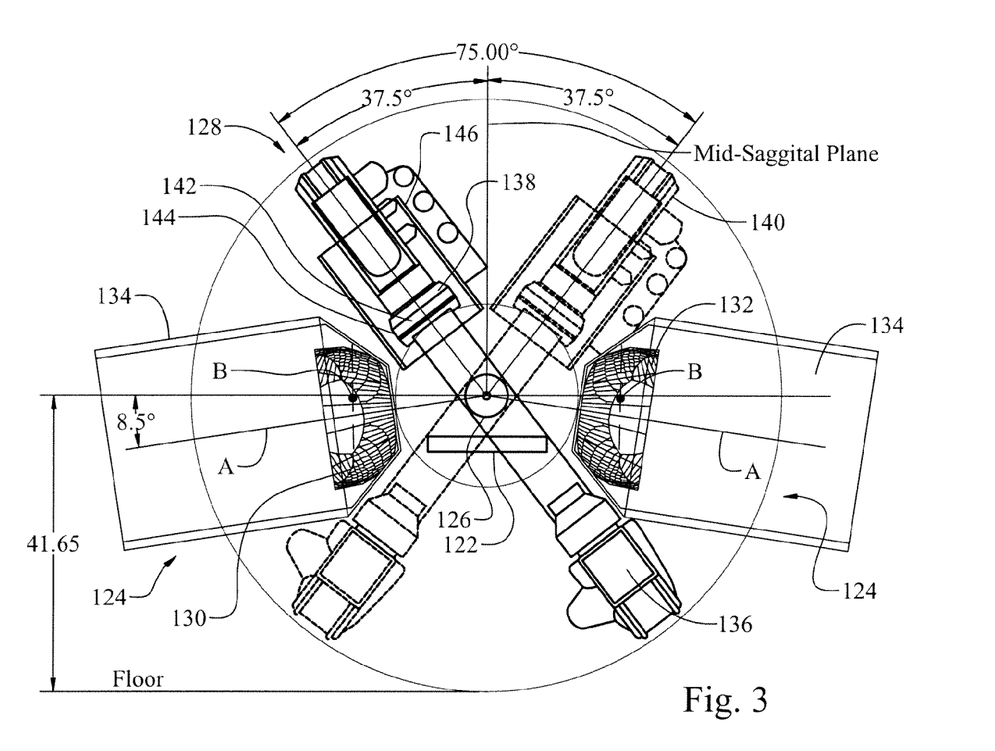
FIG. 3 is a schematic view of a second embodiment of a magnet system constructed according to the principles of this invention, showing a 75° range of motion for a C-arm carrying a 30 cm receiver.

A second embodiment of a magnetic navigation system constructed according to the principles of this invention is shown schematically in FIG. 3. The magnetic navigation system is adapted for orienting a magnetically responsive medical device in a selected direction within an operating region in a subject's body. The second embodiment of the system comprises a support 122 for supporting the subject, a magnet system 124 for applying a magnetic field to the operating region 126, and an imaging system 128 for imaging the operating region 126.

The subject support 122 is preferably a generally horizontal surface for supporting a subject in a generally horizontal position so that the operating region of the system is positioned within the subject's body.

The magnet system 124 comprises at least two magnets 130 and 132 disposed on opposite sides of the operating region 126 for applying a magnetic field sufficient for magnetic navigation in any selected direction within the operating region. Magnets 130 and 132 are preferably identical in construction. The strength of the field required for magnetic navigation depends in part upon the magnetic responsiveness of the device that is in the operating region 126, which is typically provided with a magnetically responsive element, such as a permeable or permanent magnet, or an electromagnetic device. In this preferred embodiment, the magnets 130 and 132 preferably can provide a navigating field of at least about 0.08 Tesla in any selected direction in the operating region, however in other embodiments the magnets 130 and 132 might be designed to provide a magnetic field of at least about 0.06 Tesla, or even lower as advances are made in improving the magnetic responsiveness of the medical devices deployed in the operating region 126. The magnets 130 and 132 are shaped and configured so that a change of the position and/or orientation of the magnets within an exclusion zone 134 permits the magnets to apply a magnetic field of the desired strength in the operating region 126 in any selected direction. A mechanism, not shown, is provided for repositioning and reorienting the magnets 130 and 132 as required to provide the desired field in the operating region. An example of one possible device is disclosed in U.S. patent application Ser. No. 10/347,525, for Magnetic Navigation System, incorporated herein by reference.

Each of the magnets is preferably made up of a plurality of blocks of magnetic material each of which is magnetized in one of a plurality of predetermined magnetization directions to maximize the magnet field in a particular direction at an operating point spaced from the front face of the magnet. It has been empirically determined that increments of 30° in magnetization direction are usually adequate, and any gains in field strength by obtained by smaller increments are usually not cost-effective. Details of the construction of such magnets are disclosed in U.S. Pat. No. 6,630,879, issued Oct. 7, 2003, An Efficient Magnet System for Magnetically-Assisted Surgery, and in U.S. patent application Ser. No. 10/056,227 for Rotating And Pivoting Magnet For Magnetic Navigation, the disclosures of which are incorporated herein by reference. The design of such magnets is disclosed in U.S. patent application Ser. No. 10/082,715 for Magnets With Varying Magnetization Direction and Method of Designing Such Magnets, incorporated herein by references. A possible method of manufacturing such magnets is disclosed in U.S. patent application Ser. No. 10/704,195, for Method of Making A Compound Magnet, incorporated herein by reference.

Each of the magnets 130 and 132 is sized and shaped to so that by translating the magnet along a first axis A extending radially from the operating region 26, pivoting of the magnet about a second axis B perpendicular to the first axis A and extending substantially through the center of mass of the magnet, and rotation of the magnet about the first axis A, permits the magnets 130 and 132 to apply a magnetic field to the operating region 126 in any selected direction. The translation, pivoting, and rotation of the magnets required to achieve the desired range of directions in the operating region define the exclusion zone 134 into which the imaging system 128 must not impinge so as to not interfere with the proper operation of the magnet system 124. Pivoting the magnets at or near their centers of mass helps reduce the size of the exclusion zones 134, and also allows for more compact and less expensive mechanisms for pivoting the magnets.

As shown in the Figures, the exclusion zone 134 is generally cylindrical, with a frustoconical front face oriented toward the operating region 126. The exclusion zone is preferably contained within a protective shell, which protects the mechanism for moving the magnet, and hides the movement from view.

The imaging system 128 comprises an imaging beam source 136 and an imaging beam detector 138 disposed on opposite sides of the operating region 126. The source 136 and the detector 38 are carried on a C-arm 140 which can pivot about an axis generally parallel to the longitudinal axis of the subject on the support 122, to change the imaging angle of the operating region 126. (Two C-arms are shown in FIG. 3 in order to illustrate the range of motion of the C-arm, but there is preferably only one C-arm used for imaging the operating region 126).

The detector 138 is preferably a solid state amorphous silicon x-ray receiving plate 142, which is substantially unaffected by the magnetic fields created by the magnet system 124. These solid state receiving plates are presently available in 20 cm×20 cm and 30 cm×30 cm sizes, with the 30 cm×30 cm size being shown in FIG. 3. Of course some other size imaging plate could be used. The imaging plate is disposed in a cover 144, so that the width of the imaging zone extends 15 cm on either side of the centerline between the imaging source 36 and the imaging receiver 138 for a 20 cm×20 cm plate, and so that the width of the imaging zone extends 20 cm on either side of the centerline between the imaging source 136 and the imaging receiver 38 for a 30 cm×30 cm plate.

The receiving plate 142 is preferably mounted for translation toward and away from the operating region 126, in order to change the resolution of the images of the operating region. The movement of the receiving plate 142 and cover 144 define an imaging zone 146 extending generally from the operating region 126, centered along the line between the source 136 and the receiver 138 through the center of the operating region 126. As described below the magnet system, and in particular the exclusion zones of the magnet system, preferably does not impinge upon this imaging zone 146.

The magnets 130 and 132 are configured and positioned so that the C-arm 140 can pivot through at least about 60° without impinging upon the exclusion zone of the magnets, and more specifically, so that the magnets 130 and 132 and their exclusions zones 134 don't impinge upon the C-arm 140, the imaging beam source 136 and detector 138, or the imaging zone 146. Similarly, the C-arm 140, the imaging beam source 136 and detector 138, and the imaging zone 146 do not impinge upon the magnets 130 and 132 and their exclusions zones.

As shown in FIG. 3, rather than being in direct opposition, 180° apart, the magnets 130 and 132, and more particularly the first axes A of the magnets 130 and 132 intersect at an angle of 163°. This additional 17° permits the C-arm 140 to travel a full 75°. In the preferred embodiment, this travel is preferably symmetric about the mid-sagittal plane, so that the imaging system can provide left anterior oblique and right anterior oblique images at 30° from the mid-sagittal plane.

Figure 4A:
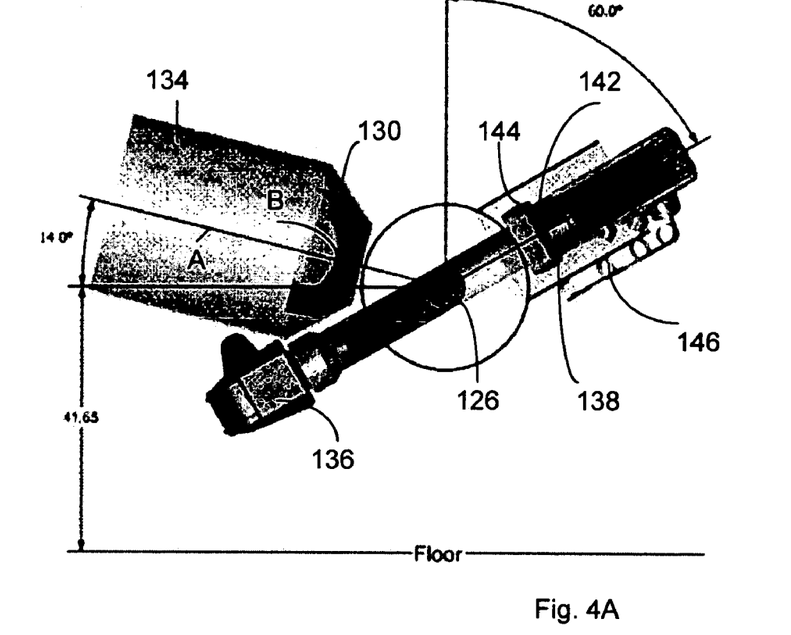
FIG. 4A is a schematic view of an alternate implementation of the second embodiment in which the magnets can rotate about the operating region, showing a 120° range of motion for a C-arm carrying a 20 cm receiver, with the magnets rotated 22.5° in one direction from its normal position.
Figure 4B:
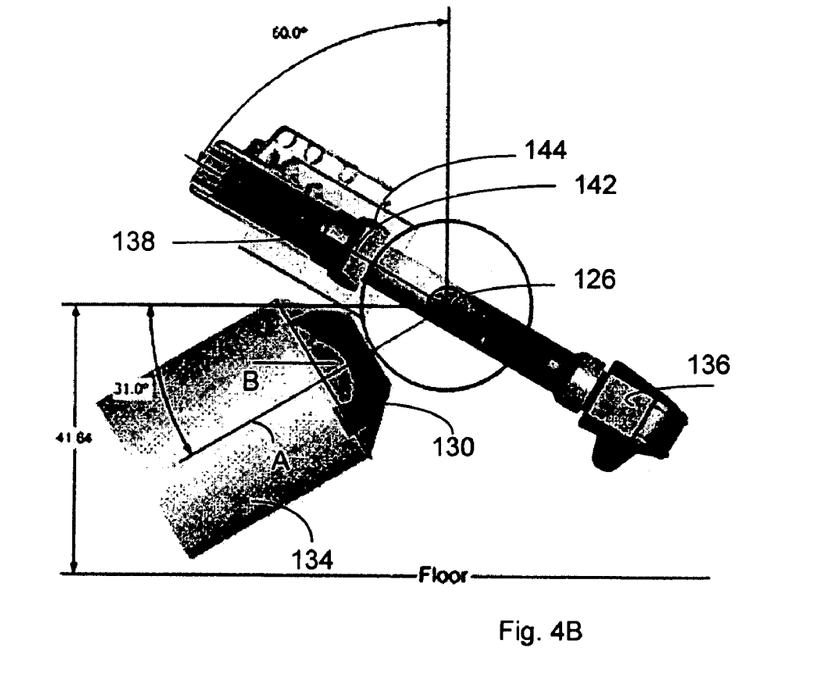

In some alternate constructions, the magnets 130 and 132 can be mounted for movement (preferably in fixed relationship to each other) about the operating region, to provide greater clearance for the imaging system to thereby extend the pivot range of the C-arm 40. As shown in FIG. 4A and FIG. 4B, the imaging system can alternatively be provided with a 20 cm×20 cm imaging plate. The smaller imaging plate 142 results in a smaller imaging zone 146, and thus permits a broader range of pivoting of the C-arm. Thus, as shown in FIGS. 4A and 4B, by permitting the magnets 130 and 132 to rotate (preferably in fixed relationship to each other) +/−22.5° about the operating region 126, the C-arm 40 can pivot over a range of 120°, preferably centered on the mid-sagittal plane. For simplicity, FIGS. 4A and 4B only show the magnet 130, it being understood that magnet 132 moves in fixed relationship with magnet 130, so that the angle between their respective A axes remains 163°.

Figure 5:
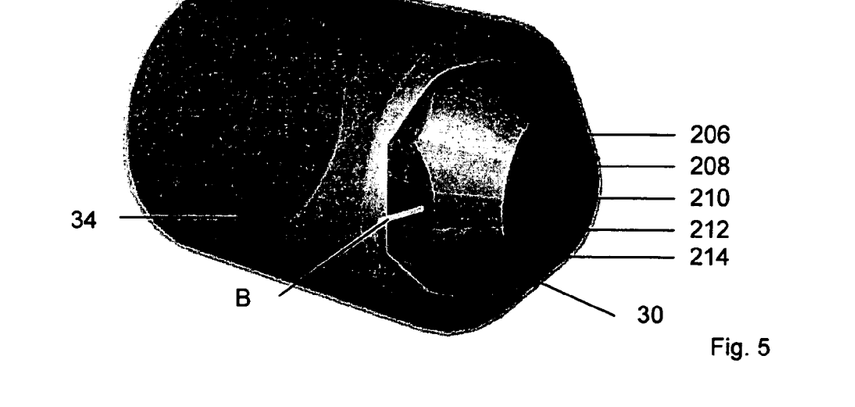
FIG. 5 is a perspective view of the magnet and its exclusion zone.
Figure 6:
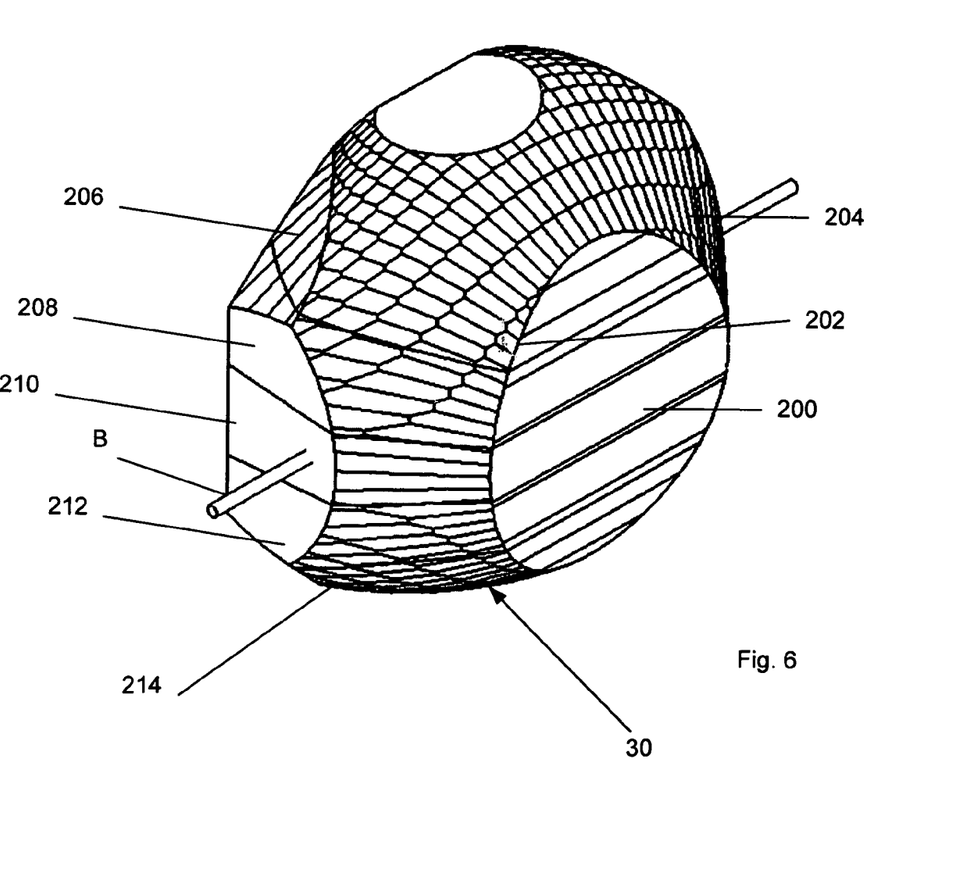
FIG. 6 is an enlarged view of the magnet.

Magnet 30 is shown in more detail in FIG. 5. As shown in FIG. 5, the magnet comprised of a plurality of sections or layers each having a different magnetization direction than the adjacent layers. As shown in FIG. 5, the magnet 30 has five layers 206, 208, 210, 212, and 214, each having a magnetization direction varying by 30° from its adjacent layers. As shown in FIG. 6. the layers 206, 208, 210, 212, and 214 extend parallel to the axis B, which extends through the center of mass 202 of the magnet 30. The magnet has a flat, generally circular front face 200, surrounded by a generally conical surface 204. The sides of the magnet 30 have a plurality of flat faces to save the weight of material that does not contribute significantly to the field strength of the magnet.

The magnetization direction of the layers 206, 208, 210, 212, and 214 varies in a plane perpendicular to the axis B. The section 206 is magnetized in a direction downwardly and rearwardly as shown in FIG. 6, at an angle of 60° with respect to vertical. The section 208 is magnetized in a direction downwardly and rearwardly as shown in FIG. 6, at an angle of 30° with respect to vertical. The section 210 is magnetized in a direction downwardly as shown in FIG. 1, at an angle of 0° with respect to vertical. The section 212 is magnetized in a direction downwardly and forwardly as shown in FIG. 6, at an angle of 30° with respect to vertical. The section 214 is magnetized in a direction downwardly and forwardly as shown in FIG. 6, at an angle of 60° with respect to vertical.

The view of FIGS. 5 and 6 is an idealized design, and in actual practice the magnet of substantially the desired shape could be built up from smaller blocks of magnetic material approximating the shape of the idealized design, as is known.

What is claimed is:

1. A magnetic navigation system for orienting a magnetically responsive medical device in a selected direction within an operating region in a subject's body, the system comprising:
    a support for supporting the subject;
    a magnet system for applying a magnetic field to the operating region, the magnet system comprising at least two magnets disposed on opposite sides of the operating region for applying a magnetic field of at least 0.08 Tesla in any selected direction in the operating region by a change of the position and/or orientation of the magnets within an exclusion zone volume;
    an imaging system for imaging the operating region, the imaging system comprising a imaging beam source and an imaging beam detector disposed on opposite sides of the operating region, the source and the detector being carried on a C-arm which can pivot about an axis generally parallel to the longitudinal axis of the subject to change the imaging angle; the magnets of the magnet system being configured and positioned so that the C-arm can pivot through at least about 60° without impinging upon the exclusion zone of the magnets.

2. The magnetic navigation system according to claim 1 wherein the C-arm can pivot at least about 30° in either direction from the midsagittal plane of the subject.

3. The magnetic navigation system according to claim 1 wherein the C-arm can pivot through at least about 75° without impinging upon the exclusion zone of the magnets.

4. The magnetic navigation system according to claim 3 wherein the C-arm can pivot at least about 37.5° in either direction from the midsagittal plane of the subject.

5. The magnetic navigation system according to claim 1 wherein the C-arm can pivot through at least about 80° without impinging upon the exclusion zone of the magnets.

6. The magnetic navigation system according to claim 5 wherein the C-arm can pivot at least about 40° in either direction from the midsagittal plane of the subject.

7. The magnetic navigation system according to claim 1 wherein the C-arm can pivot through at least about 120° without impinging upon the exclusion zone of the magnets.

8. The magnetic navigation system according to claim 7 wherein the C-arm can pivot at least about 60° in either direction from the midsagittal plane of the subject.

9. The magnetic navigation system according to claim 1 wherein each of the at least two magnets is translatable along a first axis that extends radially outwardly from the center of the operating region, is pivotable about a second axis, generally perpendicular to the first axis, that extends through the center of mass of the magnet, and is rotatable about the first axis.

10. The magnetic navigation system according to claim 9 wherein the first axes of each of the at least two magnets are collinear.

11. The magnetic navigation system according to claim 9 wherein the first axes of each of the at least two magnets form an angle of between about 163° and 178°.

12. The magnet navigation system according to claim 9 wherein the at least two magnets are rotatable about the operating region in fixed relation to move the exclusion zones out of the way of the imaging system.

13. The magnetic navigation system according to claim 1 wherein the imaging system has an imaging zone at least +/−15 centimeters on either side of the centerline between the imaging source and receiver, from the operating region to the receiver, that does not impinge upon the exclusion zone of the at least two magnets.

14. The magnetic navigation system according to claim 1 wherein the imaging system has an imaging zone at least +/−20 centimeters on either side of the centerline between the imaging source and receiver, from the operating region to the receiver, that does not impinge upon the exclusion zone of the at least two magnets.

15. The magnetic navigation system according to claim 1 wherein the exclusion zone of each of the at least two magnets is generally cylindrical exclusion zone with a frustoconical face oriented toward the operating region.

16. A magnet system for a magnetic navigation system for orienting a magnetically responsive medical device in a selected direction within an operating region in the body of a subject being supported on a support, while the operating region is being imaged with an imaging system including an imaging beam source and an imaging beam detector disposed on opposite sides of the operating region, the source and the detector being carried on a C-arm which can pivot about an axis generally parallel to the longitudinal axis of the subject to change the imaging angle, the imaging system having an imaging zone at least +/−15 centimeters on either side of the centerline between the imaging source and receiver, from the operating region to the receiver, the magnet system comprising at least two magnets disposed on opposite sides of the operating region, the magnets configured so that by changing the position and orientation of the magnets each within its own exclusion zone, the magnets provide a navigating magnetic field in the operating region of at least 0.08 T in any selected direction, such that the exclusion zone permits the C-arm of the imaging system to pivot at least 60° without the imaging zone impinging on the exclusion zone.

17. The magnet system according to claim 16 wherein the exclusion zones are sized and shaped so that the C-arm can pivot at least about 30° in either direction from the midsagittal plane of the subject.

18. The magnet system according to claim 16 wherein the C-arm can pivot through at least about 75° without impinging upon the exclusion zone of the magnets.

19. The magnet system according to claim 18 wherein the C-arm can pivot at least about 37.5° in either direction from the midsagittal plane of the subject.

20. The magnet system according to claim 16 wherein the exclusions zones are shaped so that the C-arm can pivot through at least about 80° without impinging upon the exclusion zone of the magnets.

21. The magnet system according to claim 20 wherein the C-arm can pivot at least about 40° in either direction from the midsagittal plane of the subject.

22. The magnet system according to claim 1 wherein the exclusion zones are sized and shaped so that the C-arm can pivot through at least about 120° without impinging upon the exclusion zone of the magnets.

23. The magnet system according to claim 22 wherein the C-arm can pivot at least about 60° in either direction from the midsagittal plane of the subject.

24. The magnet system according to claim 16 wherein each of the at least two magnets is translatable along a first axis that extends radially outwardly from the center of the operating region, is pivotable about a second axis, generally perpendicular to the first axis, that extends through the center of mass of the magnet, and is rotatable about the first axis.

25. The magnet system according to claim 24 wherein the first axes of each of the at least two magnets are collinear.

26. The magnet system according to claim 24 wherein the first axes of each of the at least two magnets form an angle of between about 163° and 178°.

27. The magnet system according to claim 24 wherein the at least two magnets are rotatable about the operating region in fixed relation to move the exclusion zones out of the way of the imaging system.

28. The magnet system according to claim 16 wherein the imaging system has an imaging zone at least +/−20 centimeters on either side of the centerline between the imaging source and receiver, from the operating region to the receiver, that does not impinge upon the exclusion zone of the at least two magnets.

29. The magnet system according to claim 16 wherein the exclusion zone of each of the at least two magnets is generally cylindrical exclusion zone with a frustoconical face oriented toward the operating region.

30. The magnet system according to claim 16 wherein each of the at least two magnets is comprised of a plurality of blocks each with a magnetization direction that in one a plurality of predetermined angular orientations that optimizes the magnetic field in a particular direction and an operating point spaced from the magnet.

\* \* \* \* \*

UNITED STATES PATENT AND TRADEMARK OFFICE
CERTIFICATE OF CORRECTION

PATENT NO. : 7,305,263 B2  Page 1 of 1
APPLICATION NO. : 10/801062
DATED : December 4, 2007
INVENTOR(S) : Francis M. Creighton, IV

It is certified that error appears in the above-identified patent and that said Letters Patent is hereby corrected as shown below:

Column 2, line 45: please replace - "FIG. 4A" - with -- FIG. 4B--
Column 3, line 58: please replace - "shaped to so" - with --shaped so--
Column 5, line 64: please replace - "strength by obtained" - with --strength obtained--

Column 10, line 8 (Claim 22): please replace "claim 1" - with --claim 16--
Column 10, line 44 (Claim 30): please replace "that in one a" - with --that is one of a--

Signed and Sealed this

Twenty-ninth Day of April, 2008

JON W. DUDAS
*Director of the United States Patent and Trademark Office*